United States Patent
Spreitz et al.

(10) Patent No.: US 11,427,609 B2
(45) Date of Patent: Aug. 30, 2022

(54) GLYCOSIDIC DERIVATIVES OF TREPROSTINIL

(71) Applicant: AOP ORPHAN IP AG, Vaduz (LI)

(72) Inventors: Josef Spreitz, Graz (AT); Wolfgang Strohmaier, Vienna (AT)

(73) Assignee: AOP ORPHAN IP AG, Vaduz (LI)

( * ) Notice: Subject to any disclaimer, the term of this patent is extended or adjusted under 35 U.S.C. 154(b) by 138 days.

(21) Appl. No.: 16/771,741

(22) PCT Filed: Dec. 13, 2018

(86) PCT No.: PCT/EP2018/084779
§ 371 (c)(1),
(2) Date: Jun. 11, 2020

(87) PCT Pub. No.: WO2019/115702
PCT Pub. Date: Jun. 20, 2019

(65) Prior Publication Data
US 2021/0087216 A1 Mar. 25, 2021

(30) Foreign Application Priority Data
Dec. 14, 2017 (EP) ..................... 17207329

(51) Int. Cl.
*C07H 15/24* (2006.01)
*C07C 69/708* (2006.01)

(52) U.S. Cl.
CPC .......... *C07H 15/24* (2013.01); *C07C 69/708* (2013.01); *C07C 2603/10* (2017.05)

(58) Field of Classification Search
None
See application file for complete search history.

(56) References Cited

U.S. PATENT DOCUMENTS

| 5,153,222 A | 10/1992 | Tadepalli et al. |
| 9,346,738 B2 | 5/2016 | Jain et al. |
| 9,394,227 B1 | 7/2016 | Zhang et al. |
| 2015/0166503 A1 | 6/2015 | Becker et al. |

FOREIGN PATENT DOCUMENTS

| CL | 2014003165 | 11/2014 |
| CL | 2015001535 | 6/2015 |
| CL | 2017001904 | 7/2017 |
| CL | 2019030231 | 11/2019 |
| EA | 016568 B1 | 5/2012 |
| EA | 201300892 A1 | 12/2013 |
| EP | 2792353 A2 | 10/2014 |
| EP | 3398931 A1 | 11/2018 |
| WO | 200054758 A2 | 9/2000 |
| WO | 200057701 A1 | 10/2000 |
| WO | 2003049676 A2 | 6/2003 |
| WO | 2005007081 A2 | 1/2005 |
| WO | 2013024052 A1 | 2/2013 |
| WO | 2014110491 A1 | 7/2014 |
| WO | 2016205202 A1 | 12/2016 |

OTHER PUBLICATIONS

Findlay et al., Prostaglandins, Leukotrienes and Essential Fatty Acids, 1993, 48(2), pp. 167-174. (Year: 1993).*
Findlay et al. "Radioimmunoassay for the chemical stable prostacyclin analog, 15AU81: a preliminary pharmacokinetics study in the dog." Prostaglandins, Leukotrienes and Essential Fatty Acids 48(2): 167-174 (1993).
Blackstock Guide to Biochemistry. Butterworth-Heinemann, p. 24, 1989.

* cited by examiner

*Primary Examiner* — Traviss C McIntosh, III
(74) *Attorney, Agent, or Firm* — Nixon Peabody LLP; David S. Resnick; Nicole D. Kling

(57) ABSTRACT

The present invention relates to the field of pharmaceutical products, specifically the glycosidic derivatives of treprostinil. The glycosidic treprostinil derivatives can be used to treat any conditions responsive to treatment with treprostinil, including pulmonary hypertension, such as pulmonary arterial hypertension.

21 Claims, 9 Drawing Sheets

GLYCOSIDIC DERIVATIVES OF TREPROSTINIL

CROSS-REFERENCE TO RELATED APPLICATIONS

This application is a 35 U.S.C. § 371 National Phase Entry Application of International Application No. PCT/EP2018/084779 filed Dec. 13, 2018, which claims benefit under 35 U.S.C. § 119(b) of EP Application No. 17207329.8 filed Dec. 14, 2017, the contents of which are incorporated herein by reference in their entireties.

FIELD OF THE INVENTION

The present invention relates to the field of pharmaceutical products, specifically the glycosidic treprostinil and methods for producing same.

BACKGROUND ART

Treprostinil is a vasodilator that is used for the treatment of pulmonary arterial hypertension. Treprostinil belongs to the group of prostacyclin (PGI2) analogues and is marketed under the names Remodulin (infusion), Orenitram (Oral) and Tyvaso (inhalation).

Remodulin is administered by continuous subcutaneous or intravenous infusion. According to the manufacturer, the infusion rate should initially be 1.25 ng/kg/min. If this dosage is not tolerated by the patient, the infusion rate can be lowered to 0.625 ng/kg/min.

The bioavailability is close to 100% and the biological half-life in the human organism is given as 4.4-4.6 hours [1]. Treprostinil is metabolized by the liver and urinary excretion is 79% (of which 4% unmetabolized treprostinil and 64% as identified metabolites) and feces 13%.

US 2015/166503A1 describes treprostinil derivatives.

WO 2016/205202A1 and U.S. Pat. No. 9,394,227B1 refer to treprostinil derivatives with increased systemic availability.

WO 2005/007081A2 describes treprostinil derivatives with increased oral availability.

Up to now treprostinil is still required to be administered as a continuous subcutaneous infusion or continuous intravenous infusion via an infusion pump that the patient must wear at all times. Subcutaneous infusion of treprostinil is frequently painful to the extent that the patient cannot tolerate the pain and consequently the mode of administration is switched to intravenous infusion. However, an increased risk of sepsis with intravenous Remodulin has been reported. As subcutaneous infusion is associated with pain, there is a need for developing a prostacyclin agonist or analog that can be administered by subcutaneous administration but with reduced rates of pain. Although inhaled treprostinil is more convenient and without the strong pain that is frequently associated with subcutaneously infused treprostinil, inhalation is considered to be less effective and therefore less often prescribed.

Therefore, there still exists a need to provide a more efficacious and/or more comfortable treprostinil treatment for patients.

SUMMARY OF INVENTION

It is therefore an object of the present invention to provide an improved prodrug of treprostinil. The object is solved by the subject matter of the present invention.

According to the invention, there is provided a glycoside derivative of treprostinil of general formula I,

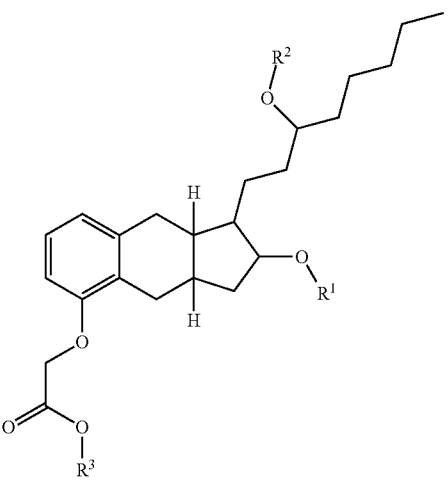

wherein
$R^1$, $R^2$ and $R^3$ are independently from one another H or a carbohydrate, and wherein at least one of $R^1$, $R^2$ and $R^3$ is not H.

In an embodiment, the glycoside derivative is of the general formula as described above, wherein $R^1$ and $R^2$ are H and $R^3$ is a carbohydrate.

A further embodiment of the invention relates to the treprostinil derivative as described herein, wherein the carbohydrate is a cyclic monosaccharide, disaccharide, oligosaccharide, an amino sugar or an alditol.

In one embodiment of the invention the monosaccharide is a pyranoside or a furanoside.

In one embodiment of the invention the carbohydrate is selected from hexoaldoses like allose, altrose, glucose, mannose, gulose, idose, galactose and talose, from hexoketoses like psicose, fructose sorbose and tagatose, from aldopentoses like ribose, arabinose, xylose, and lyxose, from ketopentoses like ribulose and xylulose, or from hexosamines, like galactosamine, glucosamine, mannosamine, neuramine acid, muramine acid, and N-acetylglucosamine.

In one embodiment of the invention the pyranoside is glucose or galactose.

A further embodiment of the invention relates to the treprostinil derivative as described herein, wherein the treprostinil derivative has a plasma half-life of at least 60 min, specifically 70 min, 80 min, 90 min, specifically of 100 min±20 min.

A further embodiment of the invention relates to the treprostinil derivative as described herein, wherein the treprostinil derivative is being cleaved in plasma in 20 h±5 h for at least 50%, specifically at least 60%, 70%, 80%, more specifically at least 90%.

A further embodiment of the invention relates to the treprostinil derivative as described herein, wherein the treprostinil derivative has reduced receptor binding affinity towards IP, EP2 and/or EP receptors compared to unmodified treprostinil. Specifically, the receptor binding is at least 2-fold, specifically 5-fold, 10-fold, 15-fold, more specifically about 20-fold reduced with regard to the receptor binding affinity of unmodified treprostinil.

One embodiment of the invention relates to a composition comprising a glycoside derivative of treprostinil as described herein.

One embodiment of the invention relates to a pharmaceutical composition comprising a glycoside derivative of treprostinil as described herein.
A further embodiment of the invention relates to the pharmaceutical composition as described herein, wherein the treprostinil derivative is selected from
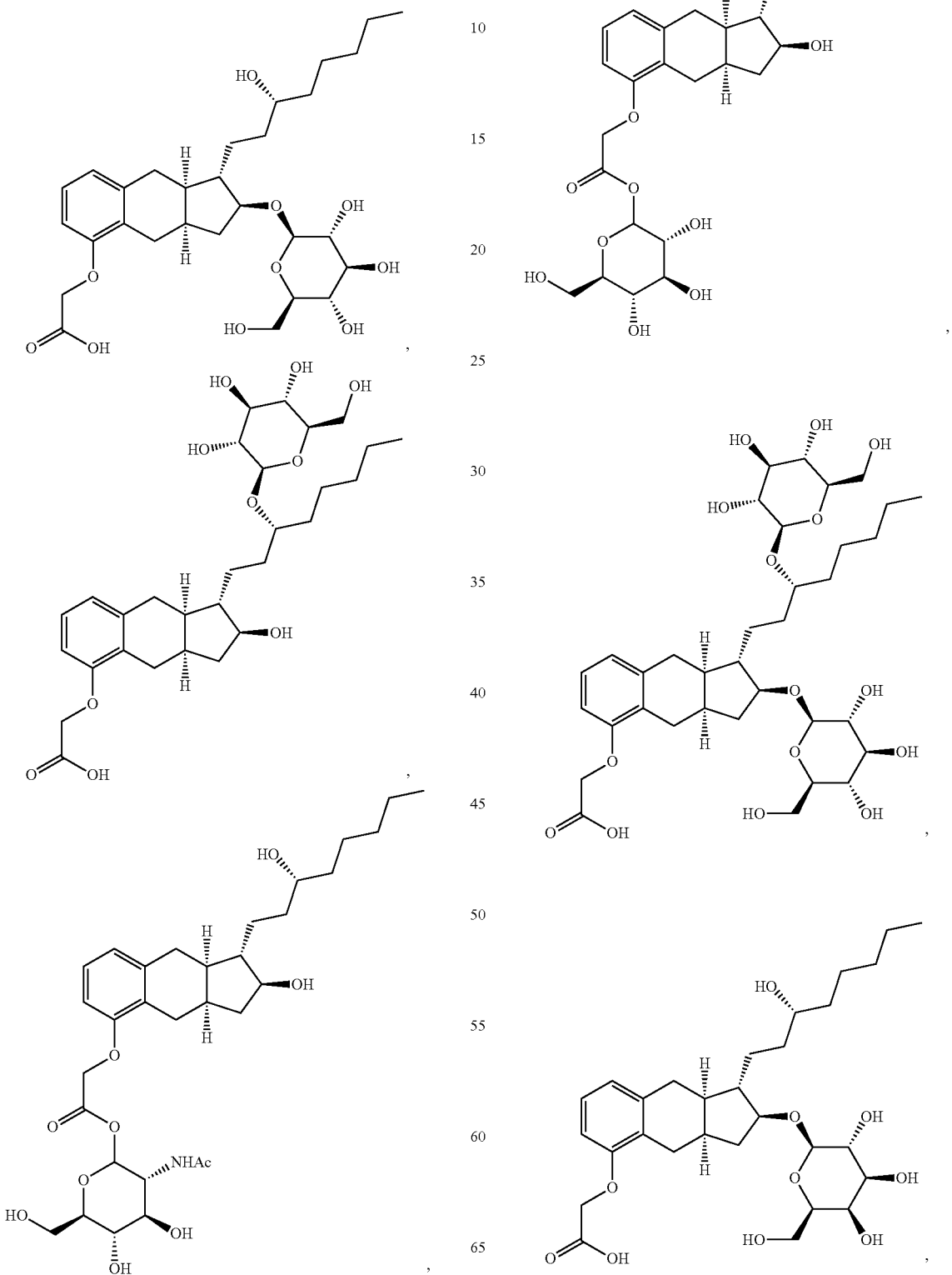

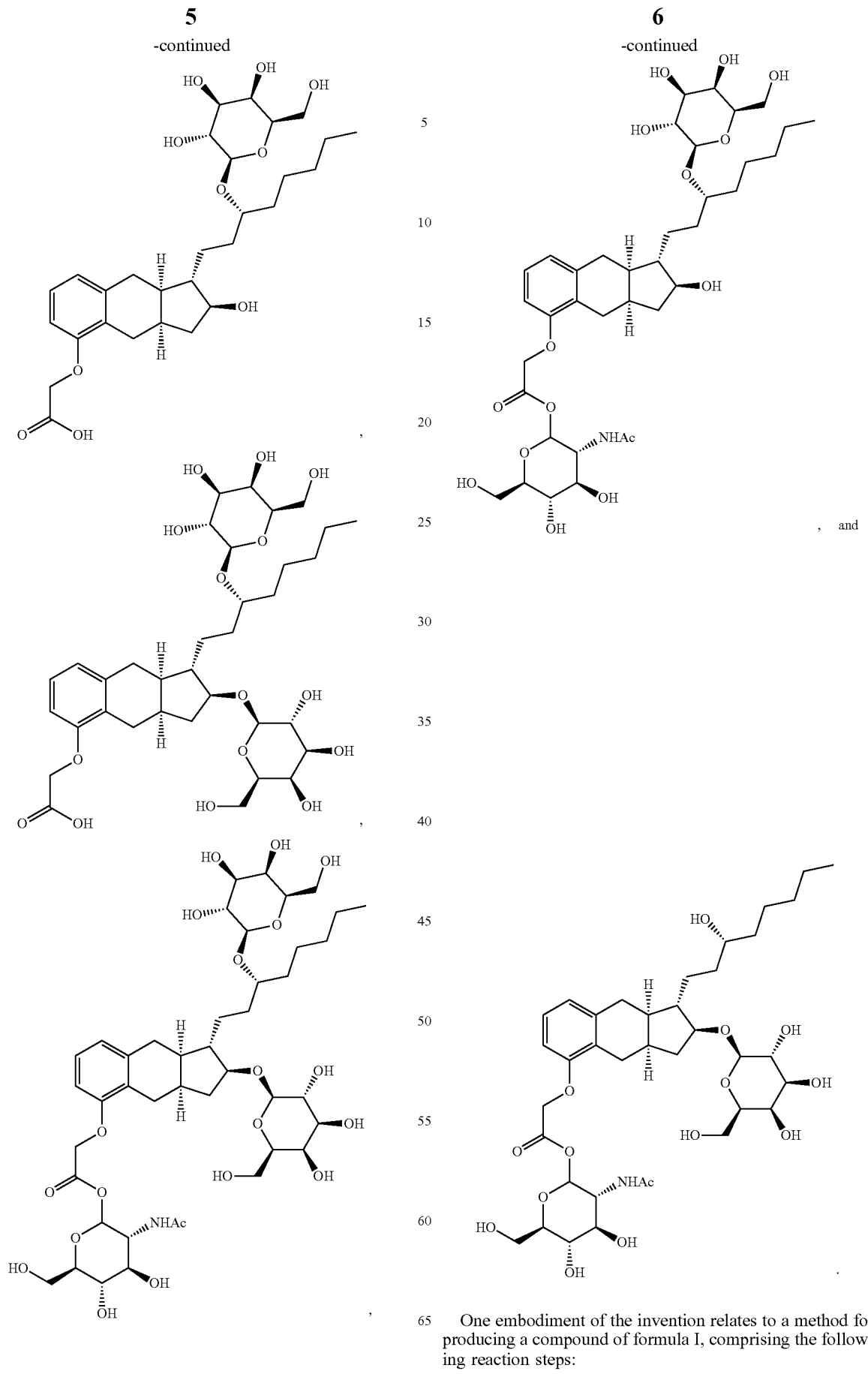
One embodiment of the invention relates to a method for producing a compound of formula I, comprising the following reaction steps:

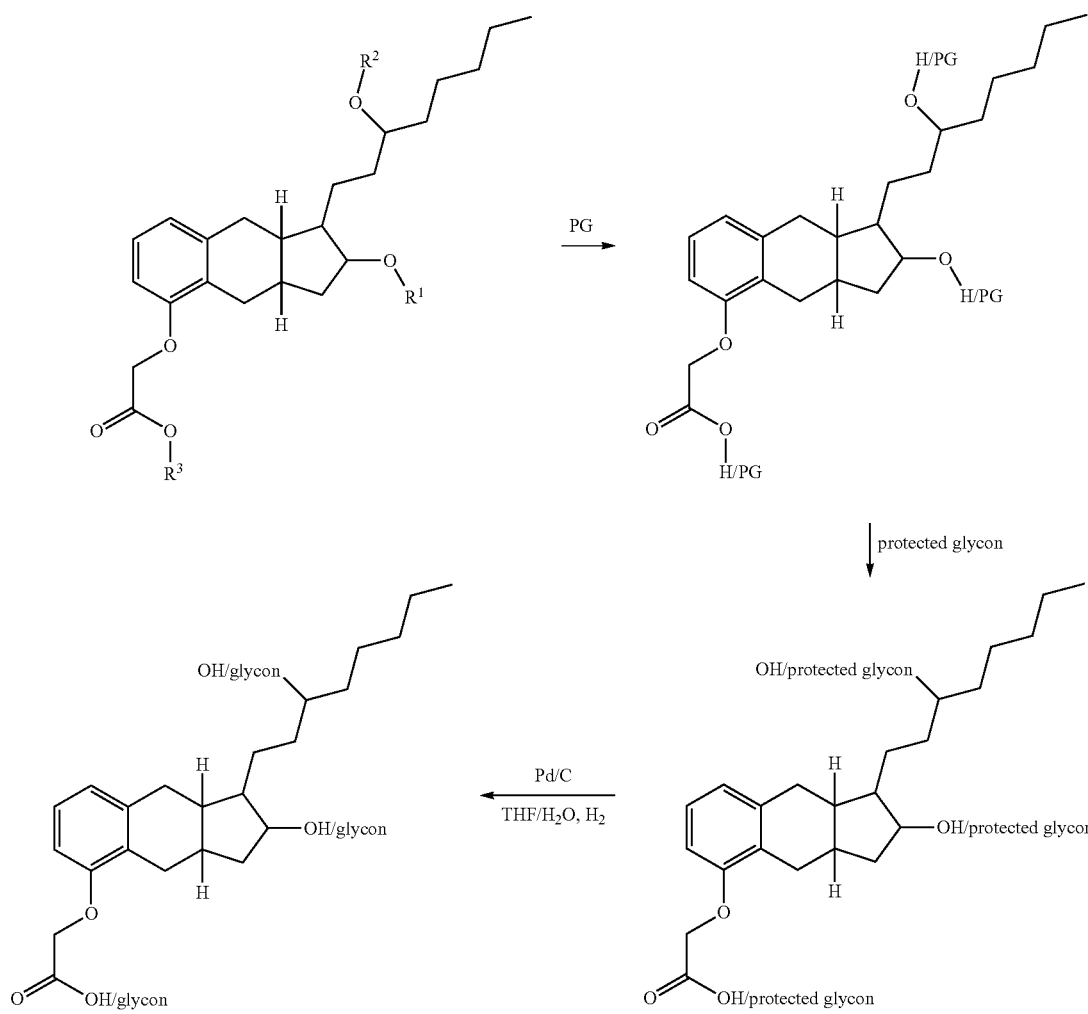

wherein PG is a protecting group, and
$R^1$, $R^2$ and $R^3$ are as defined herein.

In one embodiment of the invention one of $R^1$, $R^2$ and $R^3$ represent H and is therefore accessible for the protecting group. In the following reaction step, the non-protected residues are glycosylated. The protecting group of the glycoside is thereafter removed. Thus in the final product $R^1$, $R^2$, and/or $R^3$ are glycosylated.

A further embodiment of the invention relates to the method as described herein, wherein the protecting group is but is not limited to the group of benzyl-ether (substituted methyl ether, substituted ethyl ether, substituted benzyl ether, various silyl ethers), ester (acetate, substituted acetate, benzoate, carbonate, sulphonate), cyclic acetale, acetale from ketones and aldehydes).

Protecting groups may be preferred which are to be split off again with the highest possible protection of the molecule at room temperature, without disturbing by-products and without appreciable pH change. The use of benzyl ether is a specific embodiment herein, being easy to be synthesized and easy to be cleaved by heterogenic catalytic hydration.

Protecting groups for the acid function of treprostinil may be ester, eg benzyl ester, amides and hydrazides.

One embodiment of the invention relates to an intermediate compound of formula II,

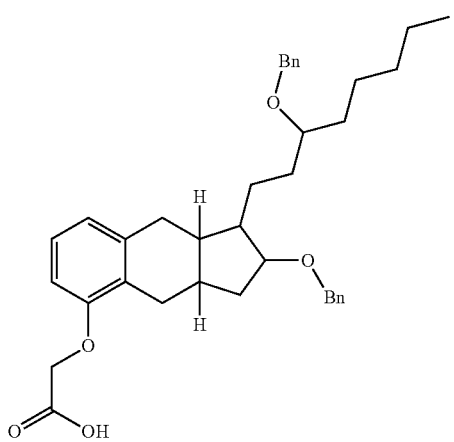

wherein Bn is a benzyl moiety.

DESCRIPTION OF EMBODIMENTS

Figure 1:
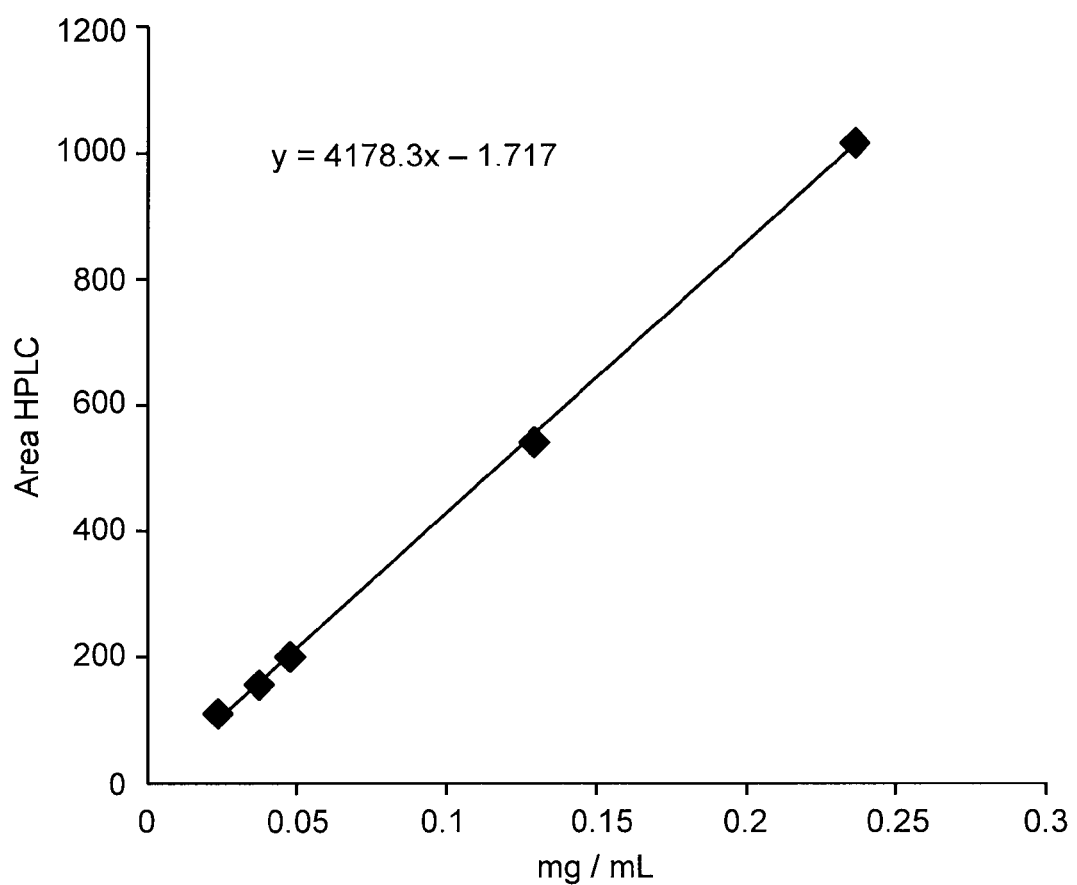
FIG. 1 depicts the calibration curve of treprostinil.

Treprostinil is a synthetic analog of prostacyclin (PGI2), indicated for the treatment of pulmonary arterial hypertension (PAH). The major pharmacologic mechanisms of action of treprostinil are direct vasodilation of pulmonary and systemic arterial vascular beds and inhibition of platelet aggregation.

Prodrugs are modified form of drugs, which on activation form drugs. Thus, prodrug design is an important part of drug discovery. Prodrugs may offer many advantages over parent drugs such as increased solubility, enhanced stability, improved bioavailability, reduced side effects, and/or better selectivity. A key step in prodrug design is the incorporation of an activation mechanism that can convert the prodrug into the active species in an efficient and/or controlled manner to meet the needs of a given medical application. Prodrug activation can be achieved through enzyme-mediated hydrolytic processes.

A growing body of evidence shows that glycosides are capable of acting as prodrugs and also to have direct therapeutic effects. Glycoside prodrugs may enable improved drug bioavailability or improved drug pharmacokinetics including more site-specific or tissue-specific drug delivery, more consistent levels of drug in the plasma, and sustained or delayed release of the drug.

Glycosides are molecules in which a sugar moiety is bound to another functional group via a glycosidic bond. Glycosides play numerous important roles in living organisms.

As used herein the term "prodrug" refers to a compound that, upon administration, must undergo a chemical conversion by metabolic processes before becoming an active pharmacological agent.

The treprostinil glycoside product is composed of two structural features: The sugar (glycon) and the treprostinil moiety (aglycon). The term "treprostinil glycoside prodrug" or "treprostinil glycoside" are used interchangeably and refer generally to the glycosides of treprostinil. The treprostinil glycoside prodrug undergoes hydrolysis of the glycosidic bond, typically by action of a glycosidase, to release the active treprostinil.

As used herein the term "glycon" refers to the sugar moiety of the glycoside. A protected glycon is a sugar moiety wherein the hydroxy group is protected by a protecting group, such as for example by a benzyl moiety.

Also in accordance with the present invention, the treprostinil glycoside prodrugs are converted upon hydrolysis of the glycosidic bond to provide the active treprostinil drug. Accordingly, the present invention has demonstrated that glycosides with a hydrophobic aglycone moiety undergo glucose hydrolysis in plasma, yielding the hydrophobic treprostinil compound.

A "carbohydrate" as used herein refers to a polyhydroxyaldehyde, or polyhydroxyketone and derivatives thereof. The simplest carbohydrates are monosaccharides, which are small straight-chain aldehydes and ketones with many hydroxyl groups added, usually one on each carbon except the functional group. Examples of monosaccharides include erythrose, arabinose, allose, altrose, glucose, mannose, threose, xylose, gulose, idose, galactose, talose, aldohexose, fructose, ketohexose, ribose, and aldopentose. Other carbohydrates are composed of monosaccharide units, including disaccharides, oligosaccharides, or polysaccharides, depending on the number of monosaccharide units. Disaccharides are composed of two monosaccharide units joined by a covalent glycosidic bond. Examples of disaccharides are sucrose, lactose, and maltose. Oligosaccharides and polysaccharides are composed of longer chains of monosaccharide units bound together by glycosidic bonds. Oligosaccharides generally contain between 3 and 9 monosaccharide units and polysaccharides contain greater than 10 monosaccharide units.

In one aspect of the invention, the carbohydrate is a sugar, in particular a hexose or pentose and may be an aldose or a ketose. A sugar may be a member of the D or L series and can include amino sugars, deoxy sugars, and their uronic acid derivatives.

Amino sugars are sugar molecules in which a hydroxyl group has been replaced with an amine group. Suitable amino sugars are for example hexosamine, galactosamine, glucosamine, mannosamine, neuraminic acid, muramic acid, N-acetylglucosamine, in particular D-glucosamine (2-amino-2-deoxy-D-glucose) or D-galactosamine (2-amino-2-deoxy-D-galactose), alditols.

In embodiments of the invention where the carbohydrate is a hexose, the hexose is selected from the group consisting of glucose, galactose, and mannose. Suitable pentose sugars include arabinose, fucose, and ribose.

The chemical structure of treprostinil possesses two hydroxyl groups which can be exploited to make glycosides through glycosidic conjugation. In some embodiments of the invention one hydroxyl group is conjugated to a sugar moiety. In some embodiments of the invention both hydroxyl groups are conjugated to sugar moieties. In some embodiments of the invention the sugar moieties are the same moieties or of different structures.

The treprostinil glycoside derivative as an O-glycoside may, for example, be obtained via chemical or via enzymatic synthesis.

In the chemical synthesis of an O-glycoside, a glycosyl donor is reacted with a free hydroxyl group in a glycosyl acceptor, generally in the presence of some promoter, to give the desired glycoside. In one embodiment of the invention, there is provided a method for producing a treprostinil glycoside, comprising reacting treprostinil with one or more glycosyl donors, optionally in the presence of some promoters to give the desired treprostinil glycoside derivative.

In accordance with the present invention, there is provided a method of producing a treprostinil glycoside, comprising incubating a treprostinil with one or more sugar donors in the presence of one or more glycosyltransferases.

Additional embodiments relate to pharmaceutical compositions comprising one or more treprostinil derivatives described herein, or a pharmaceutically acceptable salt, solvate, hydrate, or polymorph thereof, and one or more pharmaceutically acceptable excipients or carriers. The compositions can optionally contain an additional therapeutic agent.

Proper formulation may depend on various factors, such as the route of administration chosen. Potential routes of administration of pharmaceutical compositions comprising glycosidic treprostinil derivatives include without limitation oral, parenteral (including intradermal, subcutaneous, intramuscular, intravascular, intravenous, intraarterial, intramedullary and intrathecal), intracavitary, intraperitoneal, and topical (including dermal/epicutaneous, transdermal, mucosal, transmucosal, intranasal [e.g., by nasal spray or drop], intraocular [e.g., by eye drop], pulmonary [e.g., by inhalation], buccal, sublingual, rectal and vaginal). Topical formulations can be designed to produce a local or systemic therapeutic effect. Due to the glucoside derivative of treprostinil, subcutaneous administration is expected to be less painful.

As an example, formulations of glycosidic treprostinil derivatives suitable for oral administration can be presented as, e.g., capsules (including push-fit capsules and soft capsules), cachets or tablets; as powders or granules; or as boluses, electuaries or pastes. For example, push-fit capsules may contain a glycosidic treprostinil derivative in admixture with, e.g., a filler (e.g., lactose), a binder (e.g., a starch) and a lubricant (e.g., talc or magnesium stearate), and optionally a stabilizer. For soft capsules, a glycosidic treprostinil derivative can be dissolved or suspended in a suitable liquid (e.g., a fatty oil, liquid paraffin or liquid polyethylene glycol), and a stabilizer may be added.

The glycosidic treprostinil derivatives described herein can be converted to treprostinil in vivo, and thus can act as prodrugs of treprostinil. In some embodiments, glycosidic treprostinil derivatives are converted to treprostinil rapidly and substantially completely (e.g., at least about 70%, 80%, 90% or 95% conversion) in the liver.

The glycosidic treprostinil derivative can be used in conjunction with an additional therapeutic agent to treat any condition responsive to treatment with prostacyclin or treprostinil.

The therapeutically effective amount and frequency of administration of a glycosidic treprostinil derivative to treat, e.g., pulmonary hypertension may depend on various factors, including the type of pulmonary hypertension, the severity of the condition, the mode of administration, the age, body weight, general health, gender and diet of the subject, and the response of the subject to the treatment, and can be determined by the treating physician. In certain embodiments, the effective dose of a glycosidic treprostinil derivative per day is about 0.1-100 mg, 0.1-50 mg, 0.5-50 mg, 0.5-25 mg, 0.5-10 mg, 1-10 mg or 1-5 mg, or as deemed appropriate by the treating physician, which can be administered in a single dose or in divided doses. In further embodiments, the effective dose of a glycosidic treprostinil derivative per day is about 0.001-2 mg/kg, 0.005-1 mg/kg, 0.01-0.5 mg/kg or 0.01-0.1 mg/kg body weight, or as deemed appropriate by the treating physician.

EXAMPLES

The Examples which follow are set forth to aid in the understanding of the invention but are not intended to, and should not be construed to limit the scope of the invention in any way. The Examples do not include detailed descriptions of conventional methods; such methods are well known to those of ordinary skill in the art.

Example 1—Determination of Treprostinil in Plasma Samples

Usually treprostinil is determined from blood samples by HPLC-MS [2,3]. For determining treprostinil in plasma samples an isocratic, robust HPLC method was developed, which allows determining the free treprostinil in the plasma with only one step of sample preparation.

Figure 3:
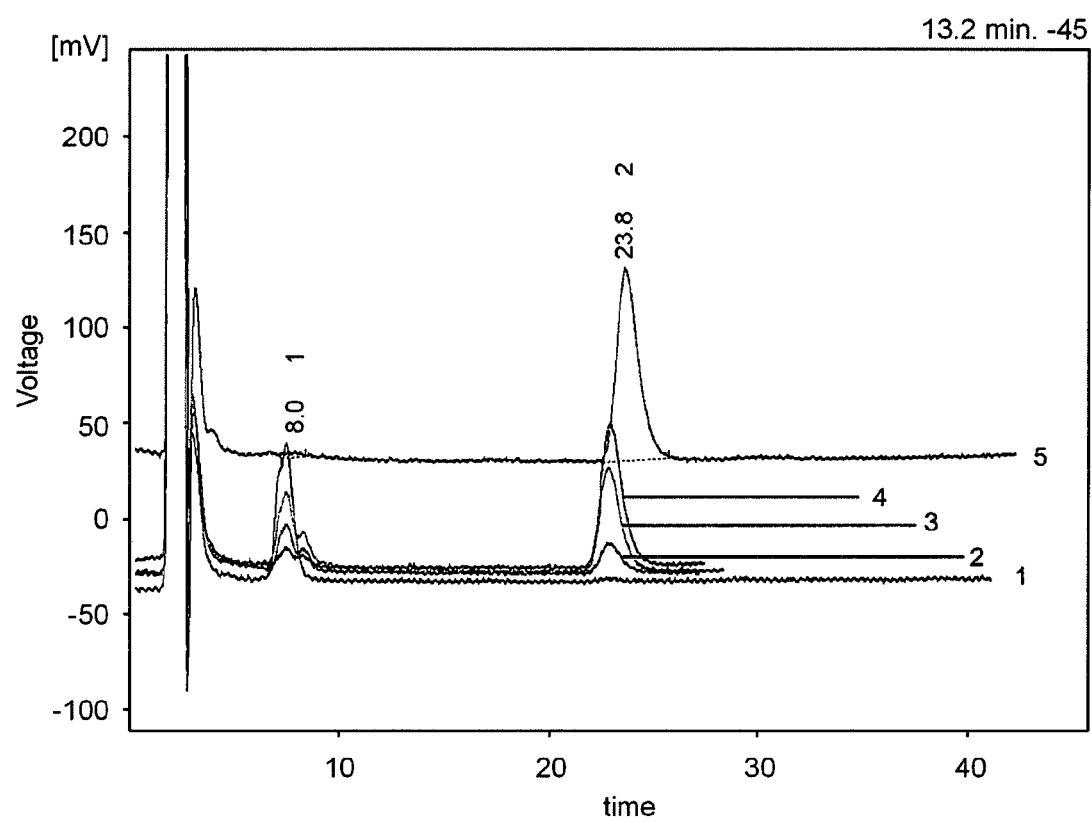
FIG. 3 represents the elution profile of free treprostinil.

HPLC method and equipment:
Pump: BESTA HD-2 400
Column oven: -
Detector: UV-VIS Beckmann 163 variable wavelength detector
Valve: Rheodyne 7125
Column: RP, Nucleosil 120 3C18, 4 mm diameter, pre-column 4 cm, column 8 cm
Sample loop: 20 µL
Detection wavelength: 277 nm
Feet rate: 0.6 mL/min
Mobile phase: 68.5 mL acetonitrile, 120 mL water, 10 mL ammonium formate, 0.2 mL HCOOH
Gradient: None, isocratic conditions; the elution profile is depicted in FIG. 3.
Calibration A calibration curve for the absolute concentration of treprostinil was generated by HPLC with the settings as defined above. The calibration curve of treprostinil is depicted in FIG. 1. The equation of the line is: $y=4178.3x-1.717$

Example 2—Hydrolysis of Treprostinil Glycoside

In order to determine if the glycoside bond of the glycosidic derivative of treprostinil is enzymatically cleaved in plasma samples.

Healthy adults (male, MW 58 years, n=2) are taken from venous blood and centrifuged (r=12 cm, 3000 rpm, 10 min). Subsequently, the plasma thus produced is stored at −20° C.

4 mg of treprostinil glycoside are provided in 10 cm test tubes. Subsequently, 4 mL of the thawed plasma are added resulting in a concentration of 1 mg/mL. Then the tubes are briefly shaken and immediately a sample (0.5 mL) drawn. The plasma sample is diluted with 3 mL absolute ethanol and the plasma proteins precipitated. Thus, the catalytic reaction is stopped immediately. The diluted samples are centrifuged (r=12 cm, 3000 rpm, 10 min) and the supernatant can be directly injected into the HPLC. Free treprostinil appears at about 23 minutes and the areas under the curve are integrated.

In parallel and simultaneously, the same process is performed with water instead of plasma to obtain the comparison to the matrix of plasma. In order to excludes acid hydrolysis in the reaction medium treprostinil galactoside is incubated in buffer solution (Sörensen pH 7), because the galactoside is slightly acidic due to the synthesis steps (around pH 6).

All preparations, treprostinil glycosides in plasma, water and buffer are now incubated in a drying oven at 37° C. Samples are taken after 0, 30, 90, 180, 270 and 1.200 minutes respectively and free treprostinil is determined by the method as described above.

Example 3—Treprostinil Glucoside

The results are shown in Table 1. The treprostinil glucoside has a plasma half-life of about 100 minutes. That means that after 100 minutes about 50% of the treprostinil glucoside is hydrolyzed. After 20 hours, the glucoside is quantitatively cleaved. 64% of the mass fraction of treprostinil glucoside is treprostinil, thus about 90% of the used treprostinil is detected. That implies that in the sample comprising treprostinil glucoside about 90% treprostinil glucoside is cleavable.

TABLE 1

Hydrolysis of treprostinil-galactoside

| Incubation time at 37° C. [min] | Area of free treprostinil in a diluted sample[1] [cm²] | | Free treprostinil in an undiluted sample[2] [mg/mL] | |
|---|---|---|---|---|
| | in plasma | in water | in plasma | in water |
| 0 | 6 | 0 | 0.009 | 0 |
| 30 | 52 | 0 | 0.087 | 0 |
| 90 | 175 | 0 | 0.29 | 0 |
| 180 | 256 | 5 | 0.43 | 0.008 |
| 1200 | 322 | 30 | 0.54 | 0.050 |

[1]Area of the treprostinil peak directly from the supernatant after centrifugation
[2]Free treprostinil converted in the incubated reaction sample mg/mL Treprostinil has a molar mass of 390.5 g/mol and treprostinil glucoside of about 552.7 g/mol. Thus, about 33% (w/w) of the glycoside is glucose. The weight of treprostinil glucoside in the reaction mixture is 1 mg/mL plasma which results in 0.33 mg glucose and 0.67 mg treprostinil (only theoretical, impurities or water are not taken into account). After 20 hours of incubation the concentration of free treprostinil is of about 0.54 mg/mL plasma. That means that the starting material consists of approximately 90% cleavable treprostinil glucoside when assuming that the glycoside has been hydrolyzed quantitatively.

Figure 2:
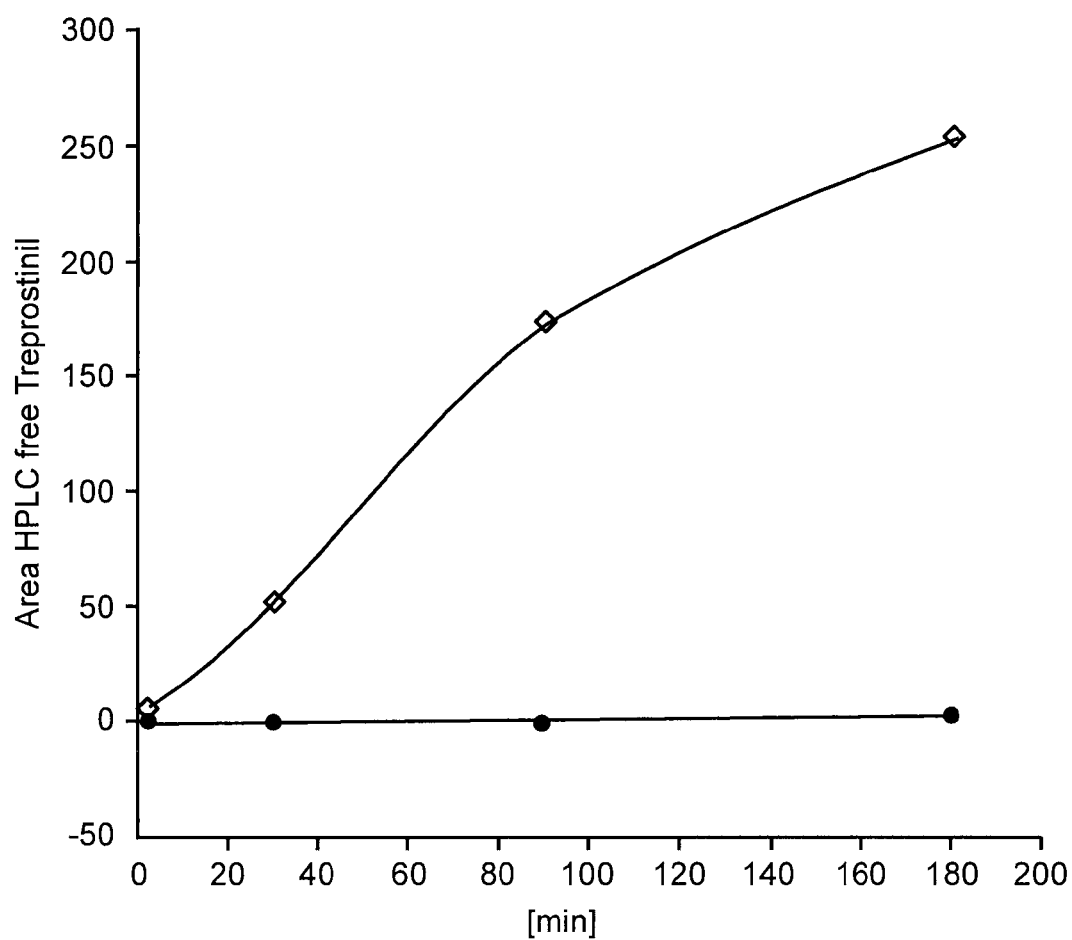
FIG. 2 shows the hydrolysis of treprostinil in human plasma and in water.

The concentration profile of free treprostinil in plasma and in water is shown in FIG. 2. The reaction essentially follows the Michaelis-Menten model, which clearly indicates an enzymatic reaction. For treprostinil glucoside, the pre-steady state phase is estimated in about 30 minutes. A balance of free treprostinil is reached in about 10 hours.
The elution profile of free treprostinil is depicted in FIG. 3. Treprostinil exhibits a retention time of 23 min. Line 1 reflects measurements after 0 min incubation time, line 2 after 30 min, line 3 after 90 min, line 4 after 180 min and line 5 after 1.200 min. The peak for treprostinil glucose appears at 8 min (line 1) and disappears over the time and is not detectable anymore after 1.200 min.

Example 4—Treprostinil Galactoside

Due to the synthesis prosecco of treprostinil galactoside, the matrix is slightly acidic in water (pH 6). Therefore, in addition to the plasma and water incubation mixture additionally incubation is also conducted in a buffer solution, e.g., Sörensen buffer at pH 7 may be used.

The results are shown in Table 2. While the half-life of the galactoside in water is not reached in the 24-hour period, the treprostinil galactoside in plasma shows a half-life of about 90 minutes. That means that 50% of the galactoside is cleaved after 90 minutes under the conditions as described above. After 20 hours, the galactoside is quantitatively cleaved into treprostinil and galactose.

Due to the manufacturing process the treprostinil galactoside used in the present methods contains about 5-6% unbound treprostinil. This amount of free treprostinil substance could also be detected by means of HPLC and is subtracted from the measured values. The values shown in Table 2 are the measured values reduced by the amount of free treprostinil contained in the starting material.

TABLE 2

Hydrolysis of treprostinil-galactoside

| Incubation time at 37° C. | Area of free treprostinil in a diluted sample[1] [cm²] | | | Free treprostinil in an undiluted sample[2] [mg/mL] | | |
|---|---|---|---|---|---|---|
| | in plasma | in water | in buffer | in plasma | in water | in buffer |
| 0 | 10 | 0 | 0 | 0.020 | 0 | 0 |
| 30 | 45 | 0 | 0 | 0.078 | 0 | 0 |
| 90 | 90 | 0 | 6 | 0.154 | 0 | 0.013 |
| 180 | 129 | 6 | 15 | 0.2193 | 0.01 | 0.028 |
| 270 | 156 | 12 | 18 | 0.2643 | 0.02 | 0.033 |
| 1200 | 180 | 15 | 73 | 0.3048 | 0.02 | 0.125 |

[1]Area of the treprostinil peak directly from the supernatant after centrifugation
[2]Free treprostinil converted in the incubated reaction sample mg/mL: each incubation mixture (plasma, water and buffer) contains 1 mg/mL treprostinil-galactoside of which X mg treprostinil is released in the corresponding time unit.

Treprostinil has a molar mass of 390.5 g/mol and treprostinil galactoside of about 552.7 g/mol. Thus, about 33% (w/w) of the glycoside is galactose. The weight of treprostinil galactoside in the reaction mixture is 1 mg/mL plasma which results in 0.33 mg galactose and 0.67 mg treprostinil. After 20 hours of incubation the concentration of free treprostinil is of about 0.304 mg/mL plasma. That means that the starting material consists of approximately 50% cleavable treprostinil galactoside. This is in line with the specification of the supplier that the remaining 50% comprising galactose (40%), free treprostinil (5-6%) and undefined residue (4-5%).

Figure 4:
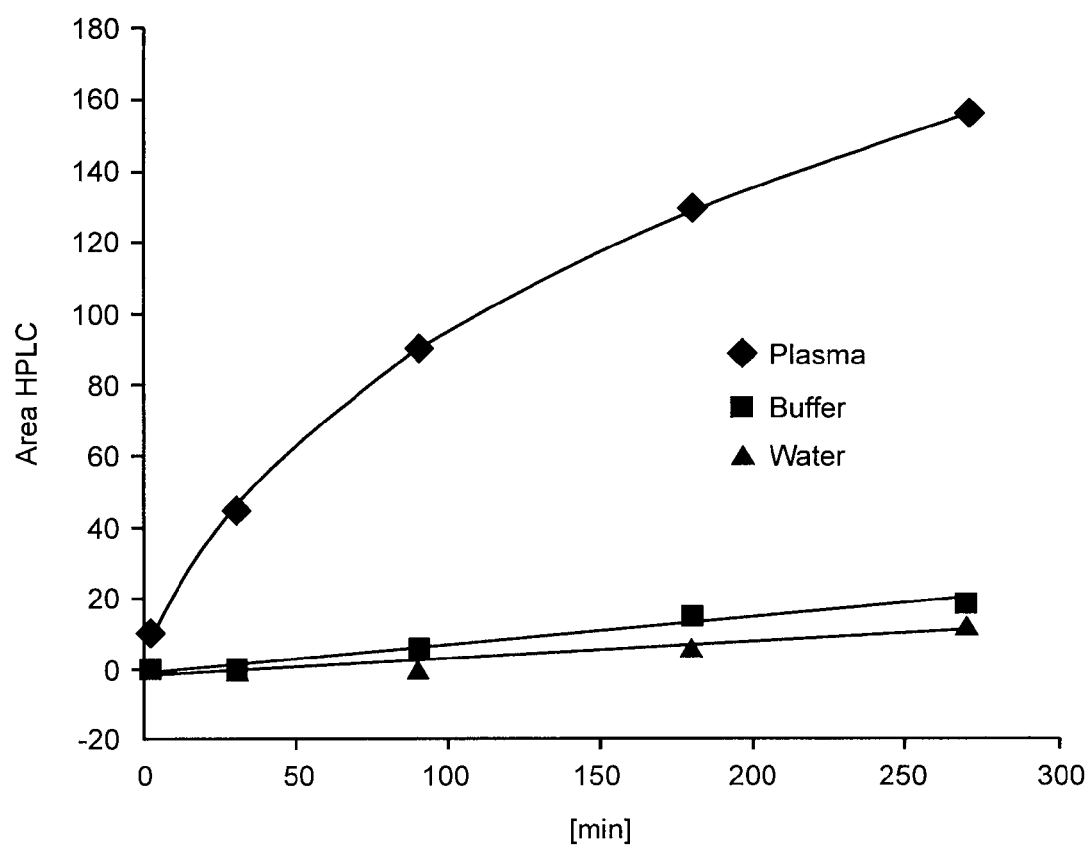
FIG. 4 shows the concentration of free treprostinil after incubation of treprostinil galactoside in human plasma.

The concentration profile of free treprostinil in plasma, buffer and water by hydrolysis of treprostinil galactoside is shown in FIG. 4. The treprostinil galactoside is quantitatively hydrolyzed in plasma after about 6-8 hours.

Example 5—Treprostinil Glucoside in Plasma

Figure 5:
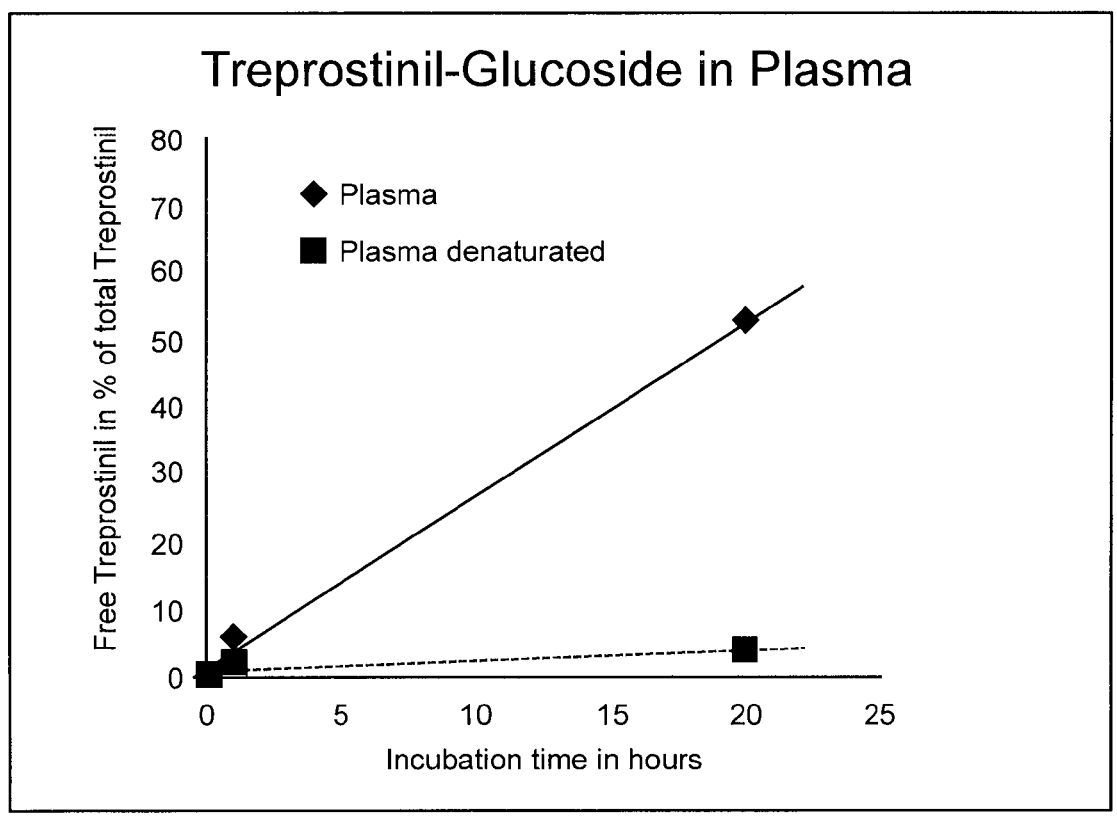
FIG. 5: Treprostinil glucoside in plasma
Figure 6:
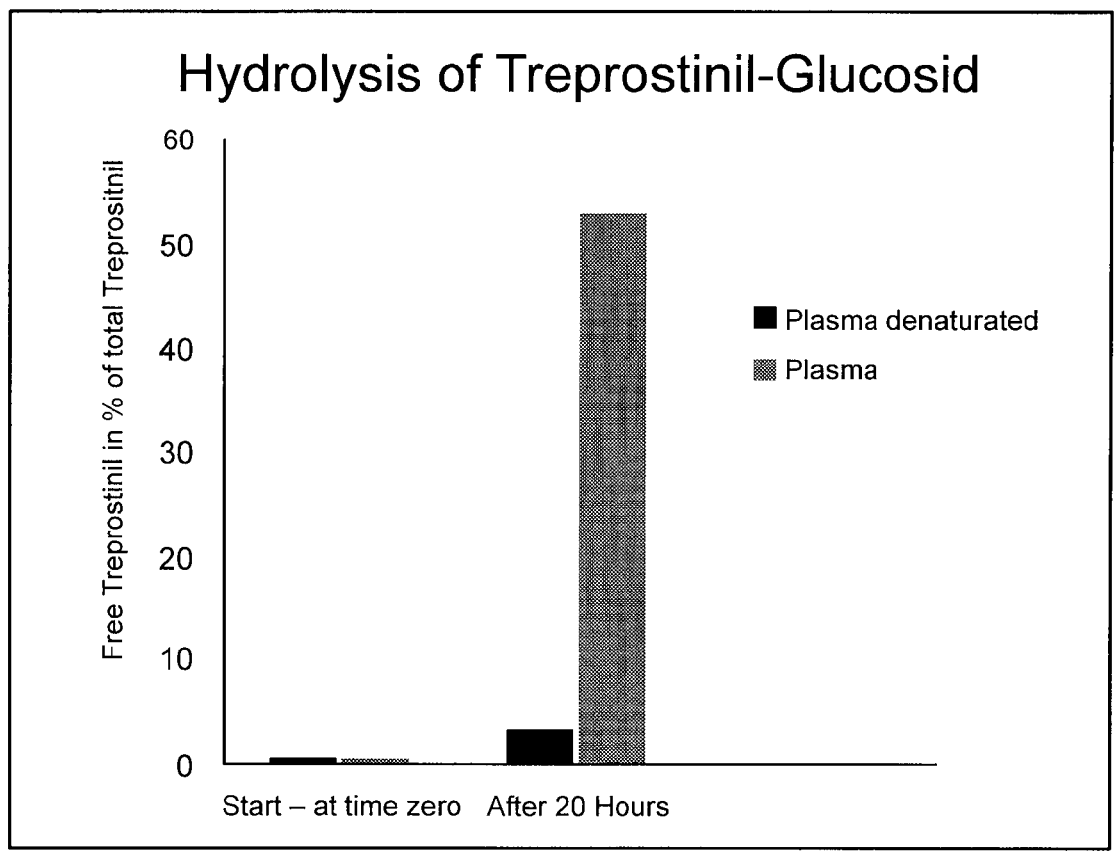
FIG. 6: Treprostinil glucoside hydrolysis in plasma

Treprostinil-Glucoside having a glucoside at the carboxyl-OH group of treprostinil was incubated in human plasma and denaturated plasma (proteins by ethanol 96%). After 20 hours of incubation time in human plasma 53% of Treprostinil-Glucoside is hydrolyzed. In contrast, only 4% hydrolyzed Treprostinil-Glucoside are detected in denaturated plasma after 20 hours. The results are shown in FIG. 5 and FIG. 6.

Example 5—Benzylester Protection of the Acid Group

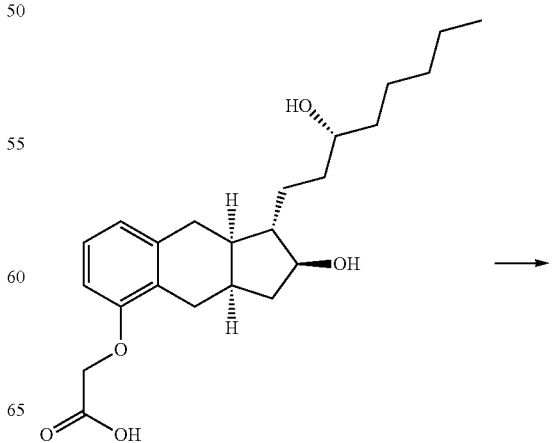

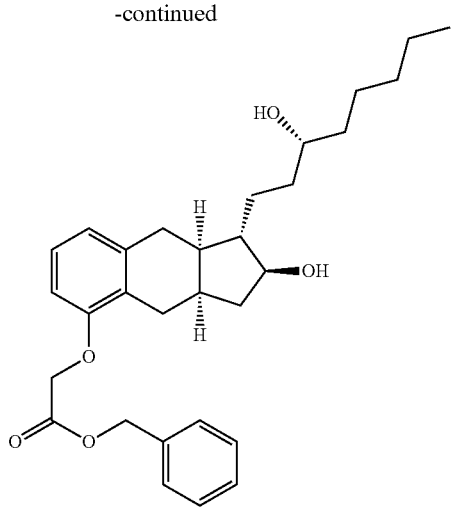

1.1 g Treprostinil sodium salt was suspended in 50 ml acetonitrile. 1.3 g of Cs$_2$CO$_3$ and 1.4 g of benzyl bromide were added to the suspension and stirred under reflux until no starting material was detectable in TLC. Then the suspension was filtered and washed with dichloromethane. The solvents were evaporated and the residue re dissolved in 50 mL of dichloromethane, washed three times with 50 mL 2% NaHCO$_3$ solution, 1×50 mL brine. Then dried over sodium sulfate filtered and evaporated to yield yellowish syrup. The syrup is re dissolved in dichloromethane, applied to a silica gel column and eluted with THF. The product containing fractions were evaporated and 1.3 g treprostinil benzyl ester as colorless syrup was obtained.

Example 6—Glycosylation of the Ester Groups

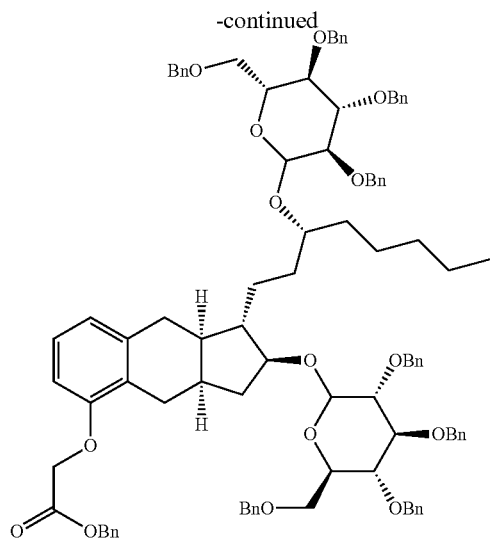

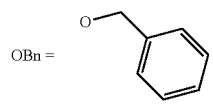

1.0 g of treprostinil benzyl ester was suspended in 20 ml THF abs. and 0.1 mL trimethylsilyl trifluoromethanesulfonate (TMSOTf) were added to the treprostinil benzyl ester solution. Then 3 g of TCA-glucose in 20 g of THF abs. were slowly added at room temperature. The reaction was quenched with 0.5 mL of trimethylamine and evaporated to yield yellowish syrup. The syrup was applied to a flash chromatography on a silica gel column. The product containing fractions were concentrated. The almost pure product was evaporated to yield 1.5 g of glycosidic treprostinil as colourless syrup.

Example 7—Removal of the Protection Group

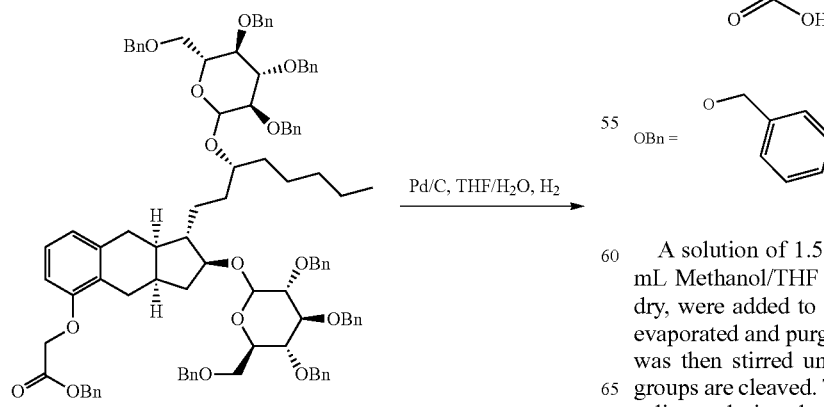

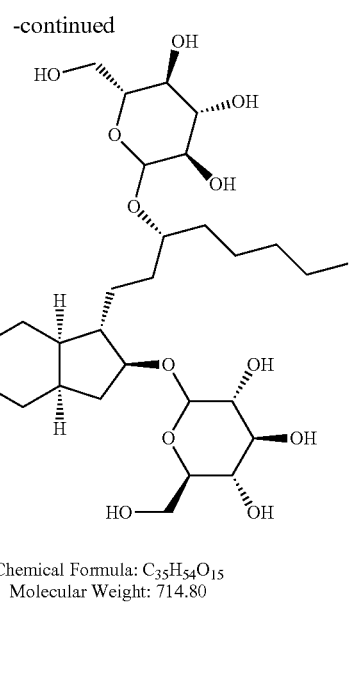

Chemical Formula: $C_{35}H_{54}O_{15}$
Molecular Weight: 714.80

A solution of 1.5 g protected treprostinil glucoside in 50 mL Methanol/THF 1:1 was prepared and 0.5 g Pd/C 10% dry, were added to the solution. The resulting mixture was evaporated and purged with hydrogen. The reaction mixture was then stirred under hydrogen at 1 bar until all benzyl groups are cleaved. Then the reaction mixture is filtered over celite and rinsed with water. The solvent is evaporated yielding the desired treprostinil diglycoside.

Example 8—cAMP Accumulation Induced by Treprostinil or Treprostinil-Glucoside in HEK293 Cells Transiently Expressing Either Prostaglandin I2 Receptor (IP), or Prostaglandin E2 Receptor 2 (EP2), or Prostaglandin E2 Receptor 4 (EP4)

Method:

Day 0: 9 million HEK293 cells were seeded on two 15 cm dishes for each experiment (for each dish: 20 ml DMEM medium+10% FCS).

Day 1: the cells were transfected with the empty vector or the plasmids encoding either IP, or EP2, or EP4 receptors. Transfection protocol: for each 15 cm dish, 10 µg of DNA and 20 µl of JetPRIME transfection reagent was added to 1 ml (final volume) JetPRIME transfection buffer and incubated for 10 min at room temperature. Thereafter the mixture was added to the cells in a dropwise manner (the medium was exchanged for the fresh medium 4 hours after the transfection to reduce the toxicity).

Day 2: the cells were washed with PBS, trypsinized, seeded on 6 well plates (0.7 million cells per well) and pre incubation with [3H]-adenine (1 µCi/ml) for 12-16 hours.

Day 3: the cells were stimulated with either Treprostinil or Treprostinil-Glucosids, having the glucoside at position $R_3$) in assay buffer (HEPES 10 mM, NaCl 120 mM, KCl 3 mM, CaCl2 2 mM, MgCl2 2 mM, Glucose 20 mM, RO-20-1724, 100 µM pH 7.3) for 30 min at room temperature (non-stimulated control was always included) and then lysed with 2.5% per chloric acid (PCA) for 30 min on ice. PCA extract was neutralized (with KOH) and [3H]-cAMP was separated from the other nucleotides by sequential chromatography using DOWEX and Aluminium oxide columns and finally the radioactivity was measured as CPM (Counts Per Minute) using a scintillation counter.

Figure 7:
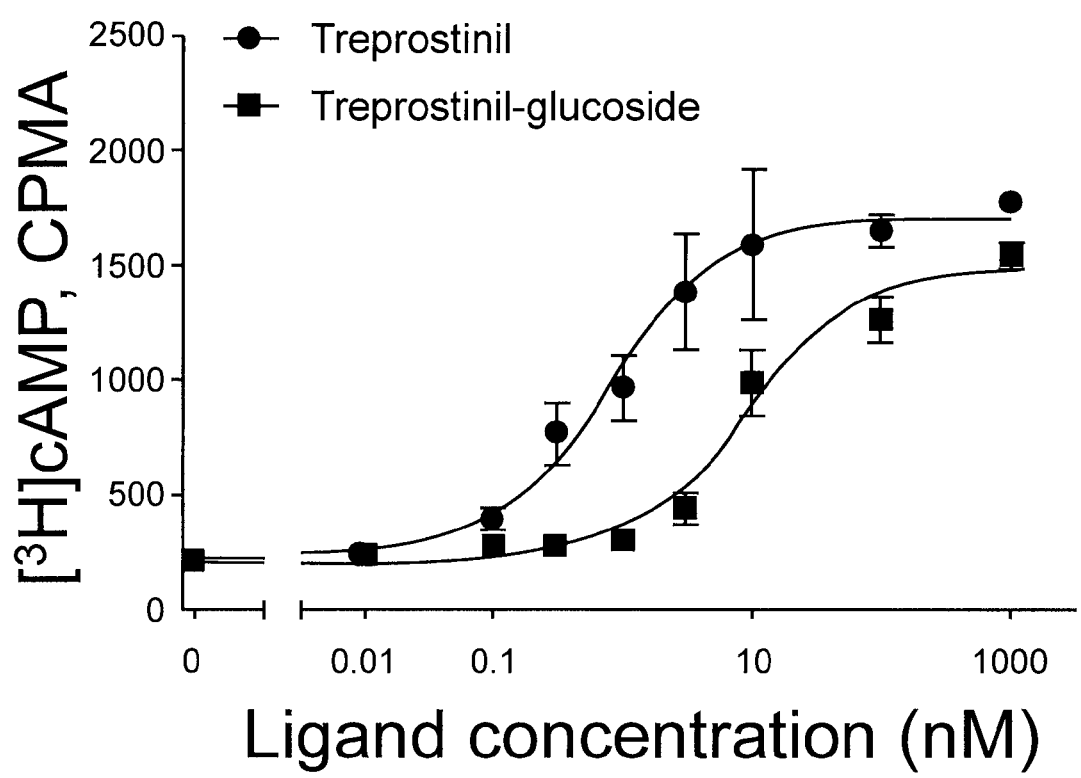
FIG. 7: Treprostinil and Treprostinil-glucoside concentration response curves in HEK293 cells transiently expressing IP receptors (n=3 independent experiments).

Treprostinil and Treprostinil-glucoside concentration response curves in HEK293 cells transiently expressing IP receptors (n=3 independent experiments) are shown in FIG. 7. The EC 50 value of Treprostinil is 0.8065, the EC50 of Treprostinil-Glucoside having the glucoside at R3 is 9.277.

Figure 8:
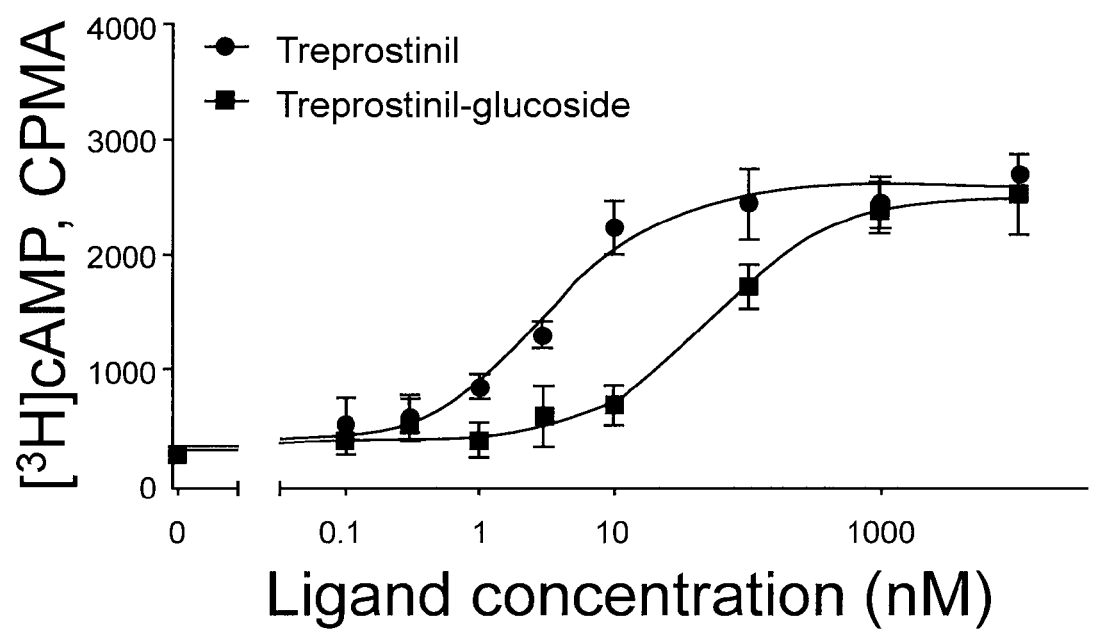
FIG. 8: Treprostinil and Treprostinil-glucoside concentration response curves in HEK293 cells transiently expressing EP2 receptors (n=4 independent experiments).

Treprostinil and Treprostinil-glucoside (having the glucoside at position R3) concentration response curves in HEK293 cells transiently expressing EP2 receptors (n=4 independent experiments) are shown in FIG. 8. The EC 50 value of Treprostinil is 3.103, the EC50 of Treprostinil-Glucoside is 56.57.

Figure 9:
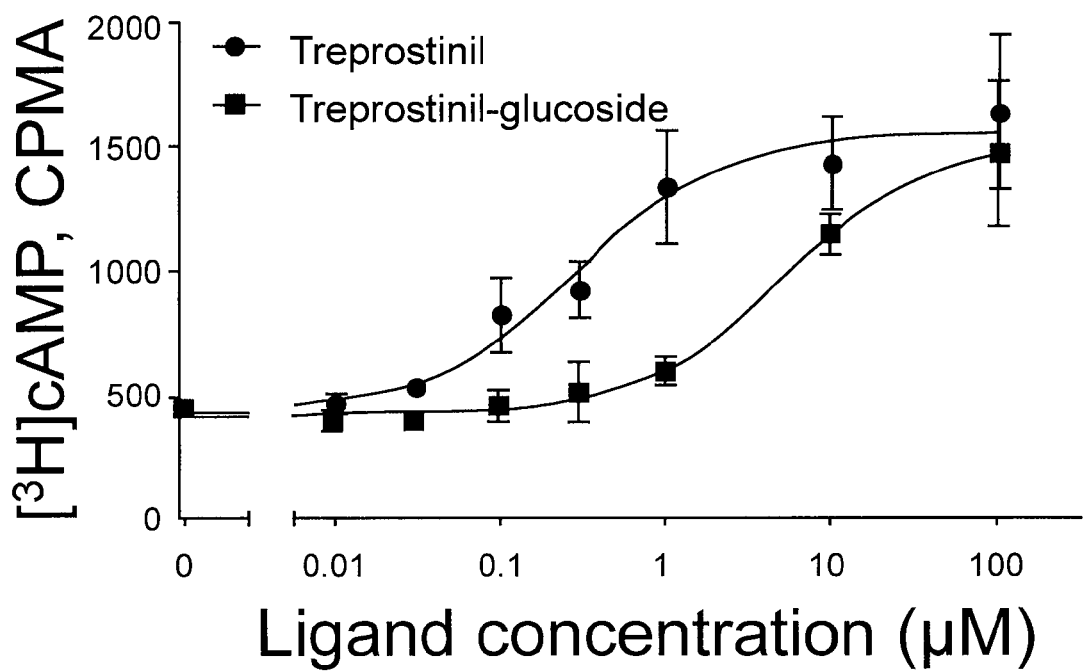
FIG. 9: Treprostinil and Treprostinil-glucoside concentration response curves in HEK293 cells transiently expressing EP4 receptors (n=3 independent experiments).

Treprostinil and Treprostinil-glucoside concentration response curves in HEK293 cells transiently expressing EP4 receptors (n=3 independent experiments) are shown in FIG. 9. The EC 50 value of Treprostinil is 0.2801, the EC50 of Treprostinil-Glucoside is 5.016.

Results: Advantageously the treprostinil-glucoside of the invention has decreased affinity towards the IP, EP2, and EP4 receptors but leads to similar cAMP increase. Thus subcutaneous administration of treprostinil-glucoside thus is expected to be less painful.

The invention claimed is:

1. A glycoside derivative of treprostinil of general formula I,

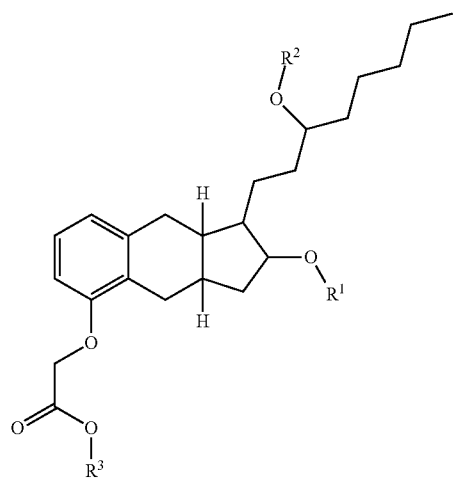

wherein $R^1$, $R^2$ and $R^3$ are independently from one another H or a carbohydrate selected from the group consisting of cyclic monosaccharides, disaccharides, oligosaccharides, an amino sugar, or an alditol, and wherein at least one of $R^1$, $R^2$ and $R^3$ is not H.

2. The glycoside derivative of treprostinil according to claim 1, wherein the monosaccharide is a pyranoside or a furanoside.

3. The glycoside derivative of treprostinil according to claim 2, wherein the pyranoside is glucose or galactose.

4. The glycoside derivative of treprostinil according to claim 1, wherein the carbohydrate is selected:
   from a hexoaldose selected from the group consisting of: allose, altrose, glucose, mannose, gulose, idose, galactose and talose;
   from a hexoketose selected from the group consisting of: psicose, fructose sorbose and tagatose;
   from a aldopentose selected from the group consisting of: ribose, arabinose, xylose, and lyxose;
   from a ketopentose selected from the group consisting of: ribulose and xylulose; or
   from a hexosamine selected from the group consisting of: galactosamine, glucosamine, mannosamine, neuramine acid, muramine acid, and N-acetylglucosamine.

5. The glycoside derivative of treprostinil according to claim 1, wherein said treprostinil derivative has a plasma half-life of at least 60 min.

6. The glycoside derivative of treprostinil according to claim 1, wherein said treprostinil derivative is at least 50% cleaved after 20 h+5h in plasma.

7. The glycoside derivative of treprostinil according to claim 1, wherein said treprostinil derivative has a plasma half-life of at least 70 min.

8. The glycoside derivative of treprostinil according to claim 1, wherein said treprostinil derivative has a plasma half-life of at least 80 min.

9. The glycoside derivative of treprostinil according to claim 1, wherein said treprostinil derivative has a plasma half-life of at least 90 min.

10. The glycoside derivative of treprostinil according to claim 1, wherein said treprostinil derivative has a plasma half-life of 100 min±20 min.

11. The glycoside derivative of treprostinil according to claim 1, wherein said treprostinil derivative is at least 60% cleaved after 20 h±5h in plasma.

12. The glycoside derivative of treprostinil according to claim 1, wherein said treprostinil derivative is at least 70% cleaved after 20 h±5h in plasma.

13. The glycoside derivative of treprostinil according to claim 1, wherein said treprostinil derivative is at least 80% cleaved after 20 h±5h in plasma.

14. The glycoside derivative of treprostinil according to claim 1, wherein said treprostinil derivative is at least 90% cleaved after 20 h±5h in plasma.

15. A composition comprising a glycoside derivative of treprostinil according to claim 1.

16. A pharmaceutical composition comprising a glycoside derivative of treprostinil according to claim 1.

17. The pharmaceutical composition according to claim 16, wherein the glycoside derivative of treprostinil is selected from

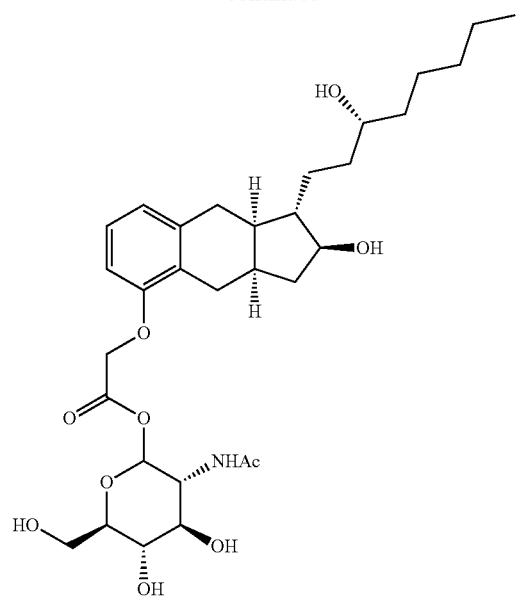

-continued

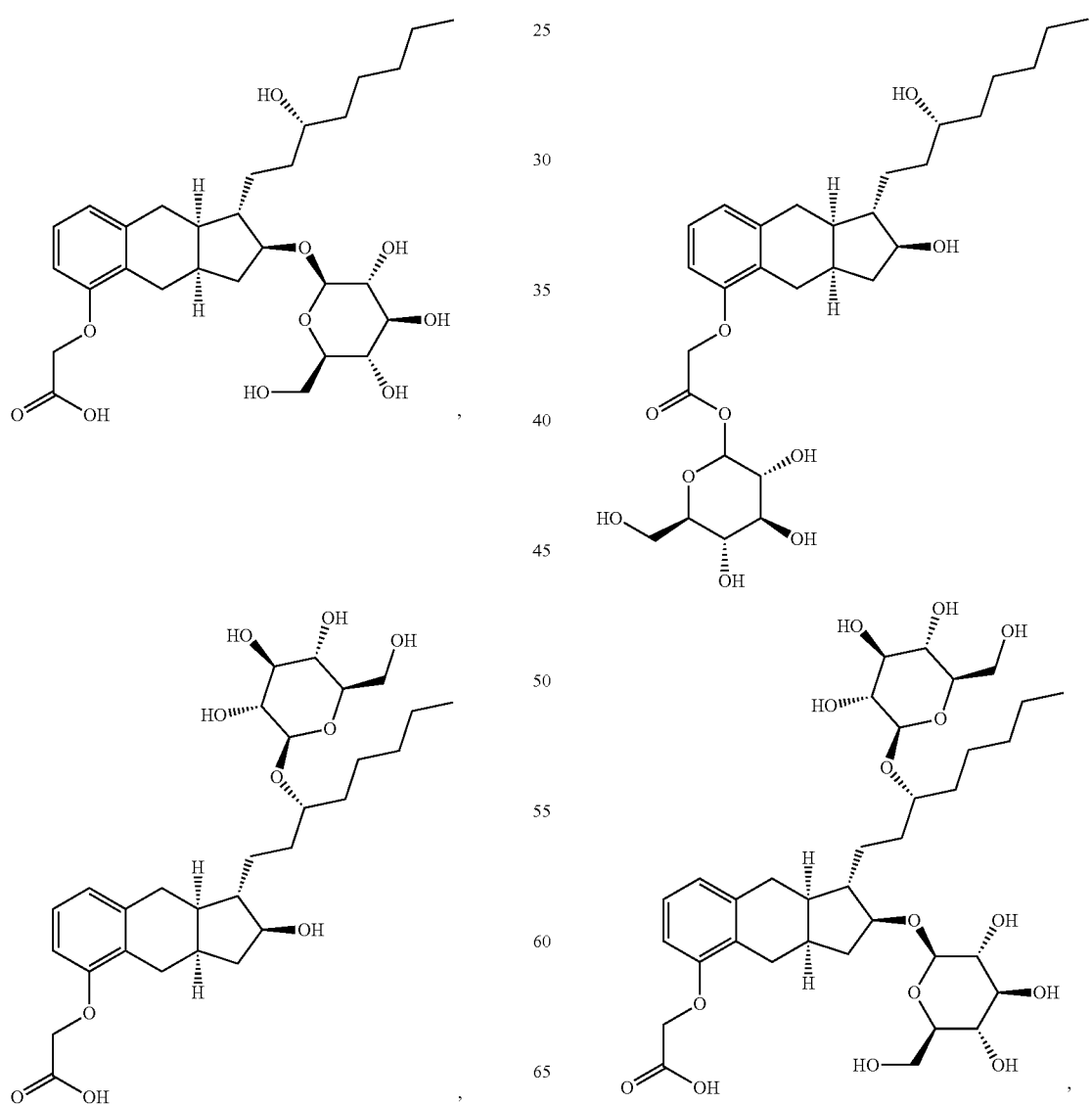

23
-continued
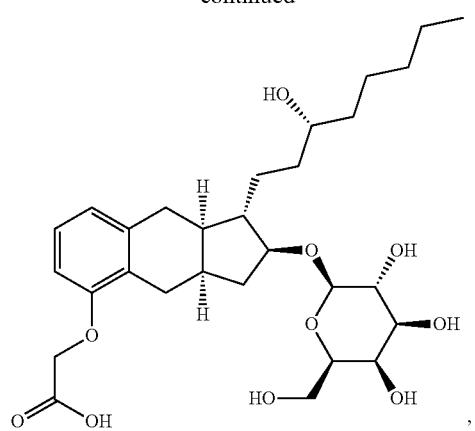
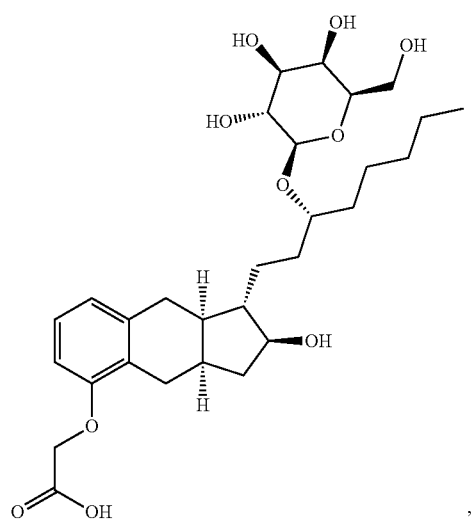
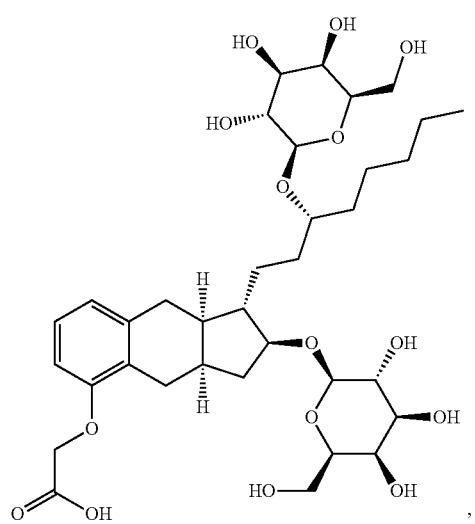
24
-continued
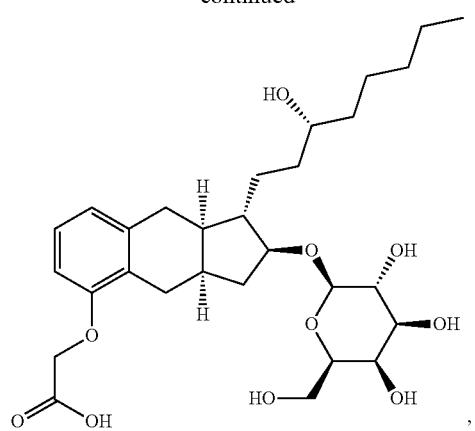
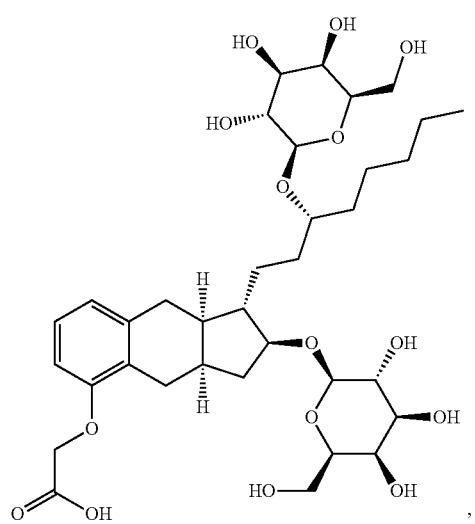
, and

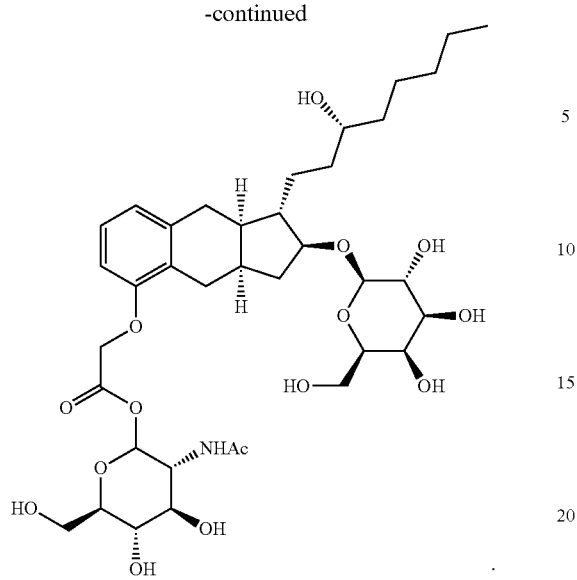
18. A method for producing a compound of formula I, wherein at least one of $R^1$, $R^2$, or $R^3$ is H, comprising the following reaction steps:
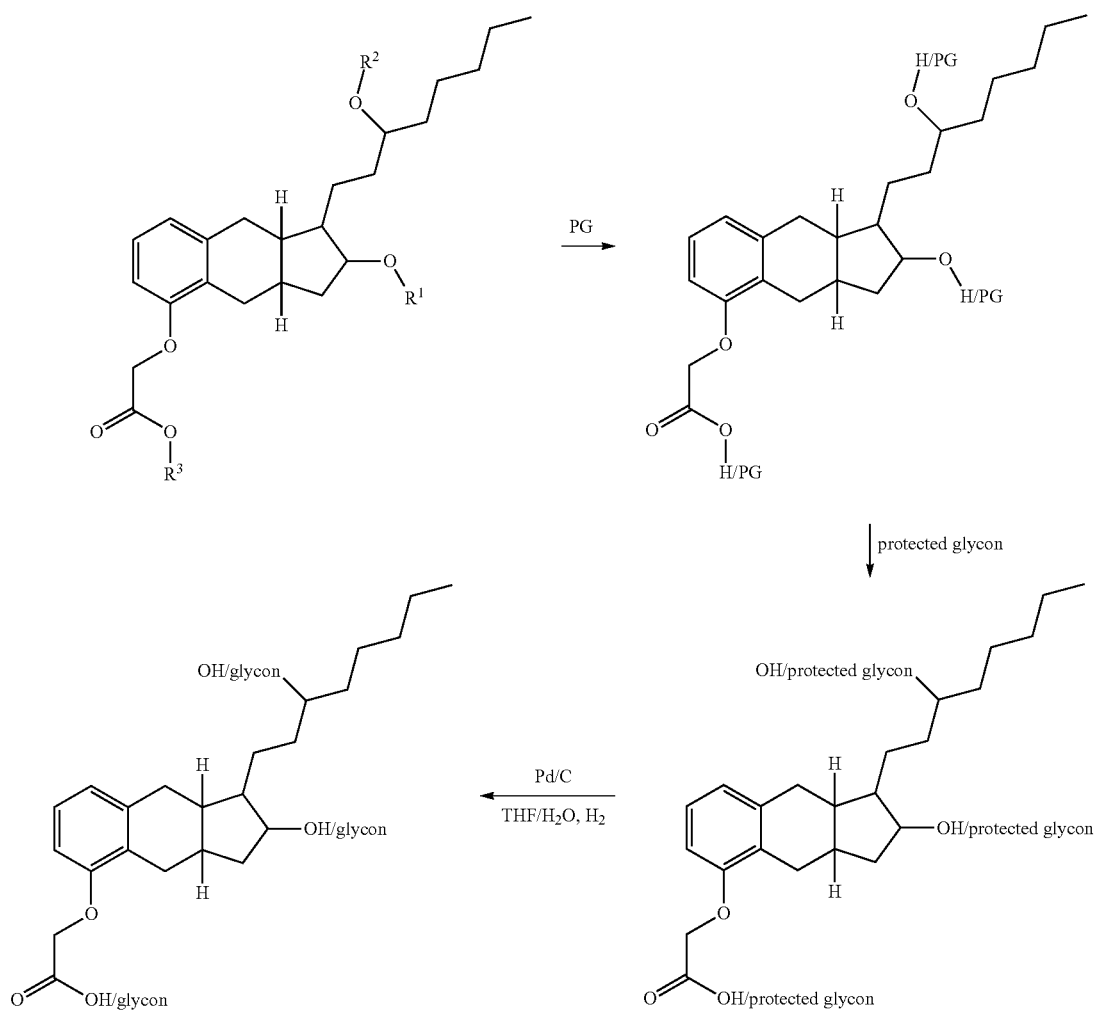

wherein PG is a protecting group, and $R^1$, $R^2$ and $R^3$ are as defined in claim 1.

19. The method according to claim 18, wherein the protecting group is benzyl, benzyl, ether selected from the group consisting of substituted methyl ether, substituted ethyl ether, substituted benzyl ether, various silyl ethers, ester selected from the group consisting of acetate, substituted acetate, benzoate, carbonate, sulfonate, cyclic acetale, acetale from ketones, ester, amide, hydracide, benzyl ester.

20. The method according to claim 18, wherein the $R^1$, $R^2$ and $R^3$ are independently from one another H, a glucose, or a galactose; and wherein at least one of $R^1$, $R^2$ and $R^3$ is not H.

21. An intermediate compound of formula II,

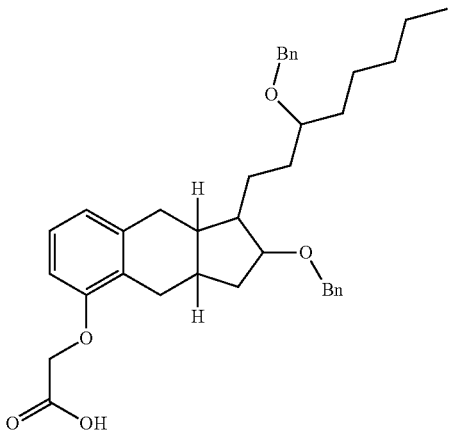

wherein Bn is a benzyl moiety.

* * * * *